(12) United States Patent
Knight

(10) Patent No.: US 11,154,699 B2
(45) Date of Patent: Oct. 26, 2021

(54) ENTERAL FEEDING CONNECTOR

(71) Applicant: Codan US Corporation, Santa Ana, CA (US)

(72) Inventor: Thomas F. Knight, Santa Ana, CA (US)

(73) Assignee: CODAN US CORPORATION, Santa Ana, CA (US)

( * ) Notice: Subject to any disclaimer, the term of this patent is extended or adjusted under 35 U.S.C. 154(b) by 401 days.

(21) Appl. No.: 15/870,788

(22) Filed: Jan. 12, 2018

(65) Prior Publication Data

US 2018/0280677 A1 Oct. 4, 2018

Related U.S. Application Data

(60) Provisional application No. 62/480,165, filed on Mar. 31, 2017.

(51) Int. Cl.
| | |
|---|---|
| *A61M 39/10* | (2006.01) |
| *A61J 15/00* | (2006.01) |
| *A61M 1/06* | (2006.01) |
| *A61J 7/00* | (2006.01) |
| *A61M 39/20* | (2006.01) |

(52) U.S. Cl.
CPC .......... *A61M 39/10* (2013.01); *A61J 15/0026* (2013.01); *A61J 7/0053* (2013.01); *A61M 1/062* (2014.02); *A61M 2039/1038* (2013.01); *A61M 2039/1072* (2013.01); *A61M 2039/205* (2013.01); *A61M 2205/6054* (2013.01); *A61M 2205/6081* (2013.01); *A61M 2205/7518* (2013.01)

(58) Field of Classification Search
CPC .......... A61M 39/10; A61M 2039/1072; A61M 2205/7518; A61M 2205/6081; A61M 2039/205; A61M 2039/1038; A61M 1/062; A61M 2205/6054; A61J 15/0026; A61J 7/0053
See application file for complete search history.

(56) References Cited

U.S. PATENT DOCUMENTS

| | | | | |
|---|---|---|---|---|
| 2014/0303601 | A1* | 10/2014 | Fangrow | A61M 39/26 604/535 |
| 2016/0089528 | A1* | 3/2016 | Schuessler | A61M 39/10 604/535 |
| 2018/0133451 | A1* | 5/2018 | Takeuchi | F16L 37/133 |
| 2018/0339132 | A1* | 11/2018 | Brunetti | A61M 25/02 |

* cited by examiner

*Primary Examiner* — Lauren P Farrar
(74) *Attorney, Agent, or Firm* — Sheppard Mullin Richter & Hampton LLP

(57) ABSTRACT

Embodiments of the application are directed toward an enteral feeding connector, comprising a stem member of a male enteral feeding connector configured to fit inside a shroud skirt of a female enteral feeding connector, wherein an end of the stem member comprises a positive taper funnel-shaped opening. In some cases, an outer radial surface of the end of the stem member is shaped to match a profile of an inner radial surface of the shroud skirt, such that the outer radial surface of the end of the stem member is flush with the inner radial surface of the shroud skirt when the stem member is disposed within the shroud skirt.

16 Claims, 13 Drawing Sheets

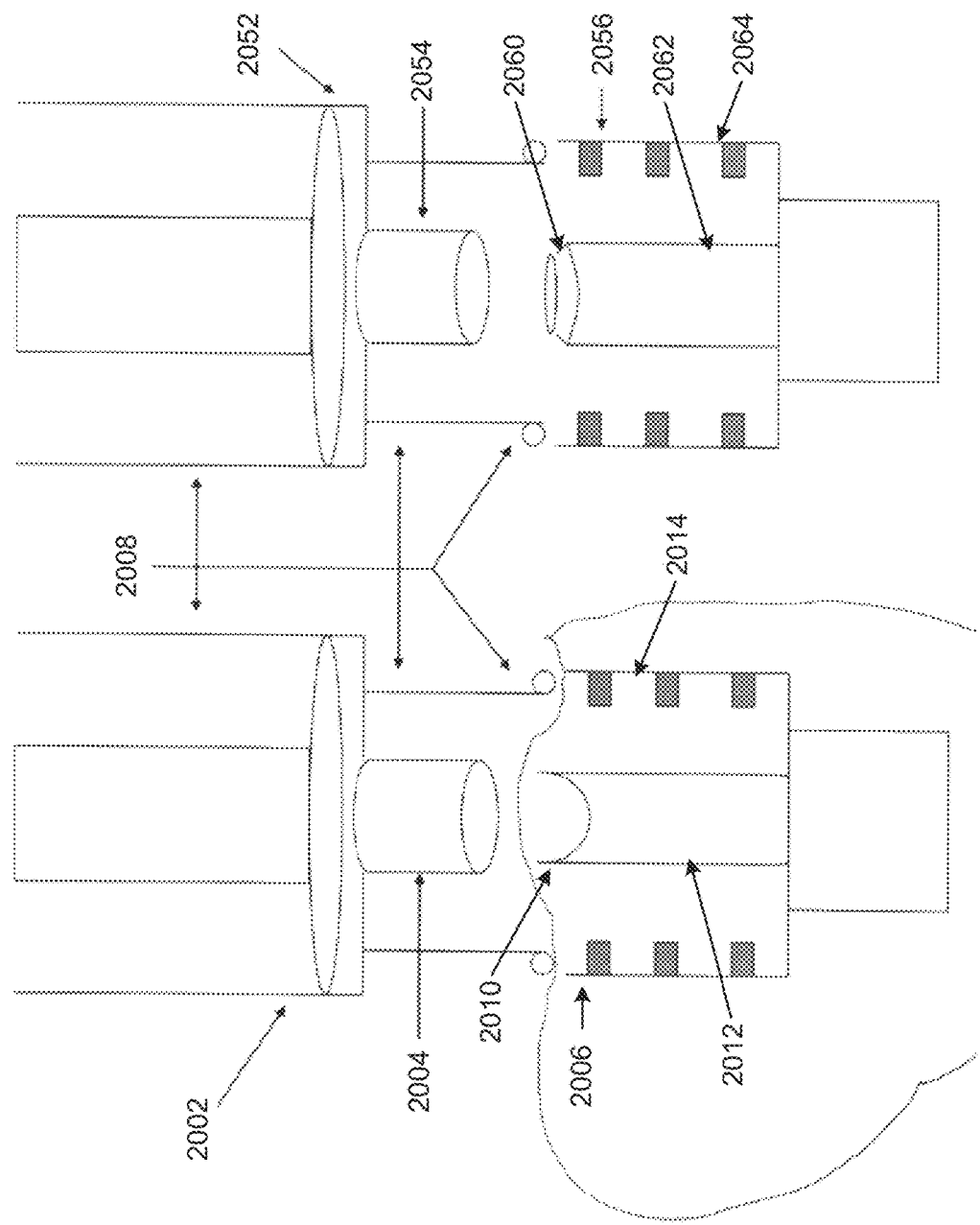

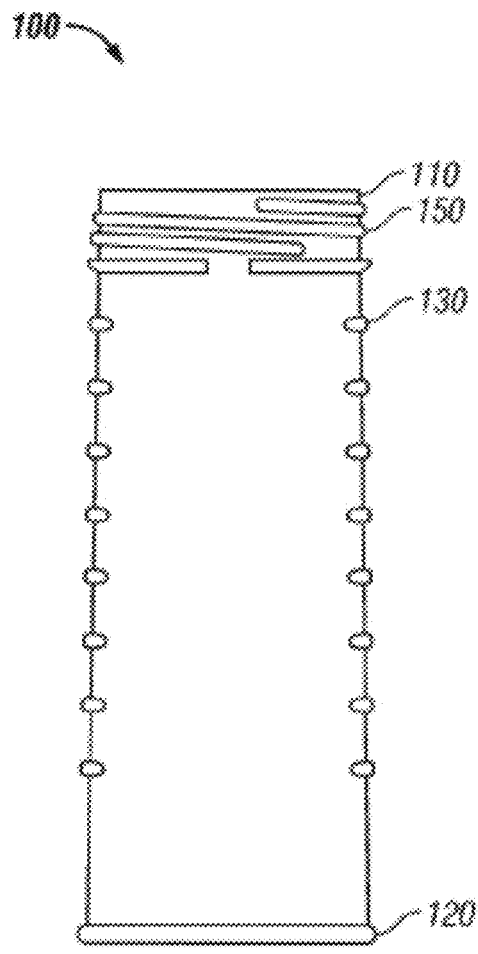
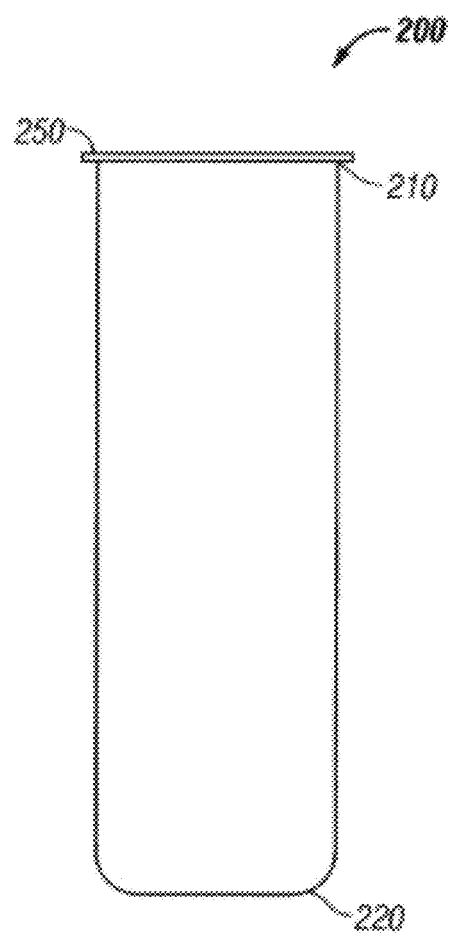
Fig. 3A
Fig. 3B

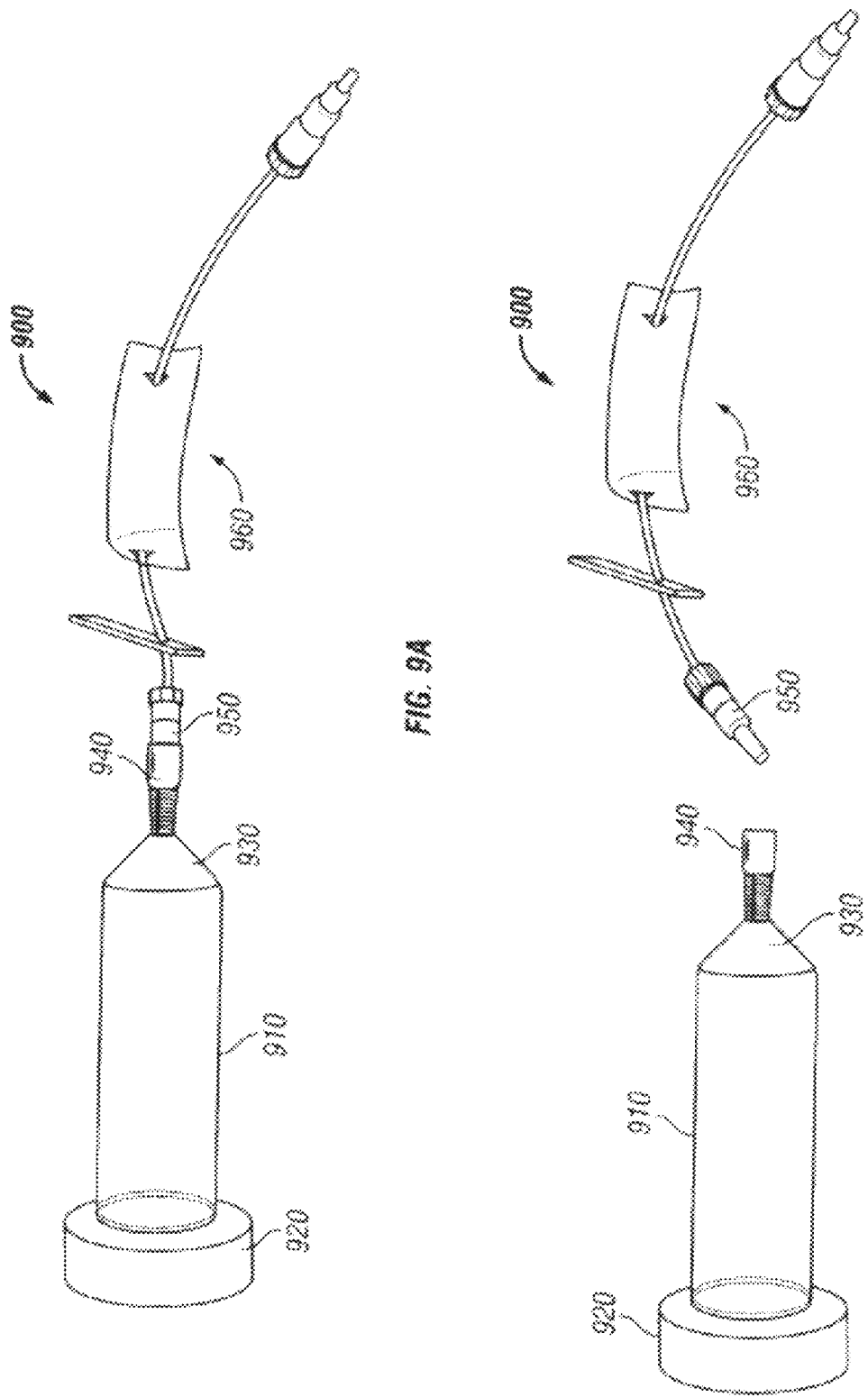

ENTERAL FEEDING CONNECTOR

RELATED APPLICATIONS

This application claims the benefit of U.S. Provisional Patent Application No. 62/480,165, filed Mar. 31, 2017, the content of which is incorporated herein by reference in its entirety

FIELD OF THE INVENTION

The present disclosure generally relates to medical devices, systems and methods and, more particularly, to enteral feeding systems and methods.

BACKGROUND

Enteral feeding is a method of providing nutrition to a person or animal that cannot or will not eat by swallowing. Enteral feeding may be done temporarily, as may be the case for temporary or acute conditions, or indefinitely, as may be the case for chronic or incurable conditions. An enteral feeding system generally includes a container for holding the feeding material and an apparatus for delivering the feeding material to the patient. One of the major issues with enteral feeding is contamination, as many of the persons or animals that are fed enterally are in a distressed or immunocompromised state. Contamination can result from various sources, but in many cases it results from exposure of the feeding material to an external environment.

Some enteral feeding systems may be used to feed babies. For example, an enteral feeding system may include a reservoir for identification, freezing, thawing, and baby delivery of breast milk or formula. A standard bottle nipple may attach to one and of the reservoir for easy oral feeding, and in an alternative embodiment, an enteral tip can be used to finish feeding through a feeding tube if the baby is unable to finish the entire amount orally. Enteral systems may be used for other types of feeding as well and are not limited to feeding babies.

Generally, a connector may be used to couple an enteral tip to the reservoir. The coupling generally may involve inserting a male connector end into a female connector end. For example, the male connector end may be threaded as to screw fit into the female connector end. In other examples, the male connector end may snap fit or form fit into the female connector end. Generally, the male connector end may have an internal taper at its distal end. In such embodiments, when the male connector end is coupled to the female connector end, a void is connected between the negative taper of the distal end of the male connector and an inner radial surface of the female connector. In such devices, the void space that is created will accumulate the liquid feeding medium as it flows between the reservoir and the enteral tip, thus creating waste and potentially allowing bacteria to crow.

BRIEF SUMMARY

The present disclosure provides systems and methods for enteral feeding a person or animal. In some embodiments, an enteral feeding system includes a reservoir body configured to hold a reservoir liner, wherein the reservoir liner is configured to hold an enteral feeding material; a reservoir connector configured to connect to the reservoir liner in a manner that permits flow of an enteral feeding material; a reservoir cap configured to connect to the reservoir body in a manner that connects the reservoir connector to the reservoir liner disposed within the reservoir body; and a syringe adapter enteral feeding assembly having a distal end configured to connect to the reservoir cap in a manner that permits flow of an enteral feeding material and a proximal end configured to connect to an enteral feeding device in a manner that permits flow of an enteral feeding material. In some embodiments, the reservoir connector includes a male stem connector with a positive taper funnel-shaped opening. The outer radial surface of the male stem connector may be uniform (i.e., no positive or negative taper), such that the outer radial surface is substantially cylindrical. An inner radial surface of the female connector may be about the same radial size as, or a small amount larger than, the radial size of the male connector. The male stem connector is configured to fit into a female shroud skirt (e.g., a female connector of a syringe). When the male stem connector is disposed within the female shroud skirt, an outer rim of the funnel-shaped stem opening contacts an inner-edge of the female shroud skirt, fluid may flow between the reservoir and the device connected to the reservoir (e.g., the syringe) without being caught or redirected into void spaces between the reservoir and the connected device (i.e., no such void spaces will be created because the outer radial surface of the male connector will be flush with the inner radial surface of the female connector and fluid will transfer between the reservoir and enteral tip through the positive taper funnel-shaped opening of the male connector.

In some embodiments the reservoir liner is pre-filled with an enteral feeding material and sealed. In some such embodiments the reservoir cap is configured to pierce or open the reservoir liner pre-filled with an enteral feeding material. In some embodiments the system also includes an enteral feeding device. In some such embodiments the enteral feeding device is selected from the group consisting of a nasogastric feeding tube, a gastric feeding tube, jejunostomy tube, and a gastrojejunostomy tube. In certain embodiments the syringe adapter enteral feeding assembly is configured to connect only to an enteral feeding device. In some embodiments the syringe adapter enteral feeding assembly is configured to connect only to enteral feeding elements.

In some embodiments, the enteral feeding system includes a reservoir body configured to hold a reservoir liner, wherein the reservoir liner is configured to hold an enteral feeding material; a reservoir connector configured to connect to the reservoir liner in a manner that permits flow of an enteral feeding material and prevents substantial exposure to an external environment; a reservoir cap configured to connect to the reservoir body in a manner that permits flow of an enteral feeding material and that connects the reservoir connector to the reservoir liner disposed within the reservoir body in a manner that prevents substantial exposure to the external environment; and a syringe adapter enteral feeding assembly having a distal end configured to connect to the reservoir cap in a manner that permits flow of an enteral feeding material and prevents substantial exposure to the external environment, and a proximal end configured to connect to an enteral feeding device in a manner that permits flow of an enteral feeding material and that prevents substantial exposure to the external environment. In various embodiments the reservoir liner is pre-filled with an enteral feeding material and sealed. In some such embodiments the reservoir cap is configured to pierce or open the reservoir liner pre-filled with an enteral feeding material. In certain embodiments the system also includes an enteral feeding device. In some such embodiments the enteral feeding device is selected from the group consisting of a nasogastric feeding tube, a gastric feeding tube, jejunostomy tube, and a gastrojejunostomy tube. In certain embodiments the syringe adapter enteral feeding assembly is configured to connect only to an enteral feeding device. In some embodiments the syringe adapter enteral feeding assembly is configured to connect only to enteral feeding elements.

Embodiments disclosed herein further provide a method for delivering an enteral feeding material to a patient. In certain embodiments, the method includes the use of a system as described herein. In some embodiments, a method for delivering an enteral feeding material to a patient includes an enteral feeding medium that is not substantially exposed to an external environment.

In some embodiments, the enteral feeding system features a capped reservoir comprising a one-piece bottle with no vent holes. The capped reservoir includes a top end having a threaded section dimensioned to mate with a threaded cap. The threaded cap provides a leak proof seal when tightened on the threaded section of the bottle, and allows venting of the bottle when loosened. Because the enteral feeding system comprises a closed system, venting is needed to allow the fluid to flow. The cap may be tethered to the bottle such that it is not misplaced. The bottom end of the one-piece bottle terminates in a funneled connector port, which may provide connections (e.g., through the use oral syringe connectors) in a manner that is not compatible with IV connections. The one-piece bottle and cap may be made from a suitable material such as plastic. The plastic may be clear, partially transparent, white, orange, purple, or any other suitable color. In certain embodiments, a stand having a center hole for slidably receiving the one-piece bottle may be provided for supporting the bottle in an upright position. the stand may comprise a plurality of legs, or, alternatively, may comprising a one-piece mold.

In further embodiments, the one-piece bottle includes a cap having a filtered air vent port that may be selectively closed, for example, using a snap-fit seal. Alternatively, the selectively closable vent port may be non-filtered. In some embodiments, the closable air vent port may be located on the side of the bottle rather than on the cap. During use, the closable vent port provides air compensation when opened, and provides a leak proof seal when closed. In embodiments featuring a filtered vent port, the air filter may or may not comprise a bacterial barrier. By way of example, the filter may comprise a 0.2 micron filter for air filtration providing significant bacterial protection.

In additional embodiments, the one-piece bottle includes a novel vented cap that prevents bacteria from entering the bottle. The vented cap allows the bottle to be filled with breast milk through the use of a breast pump that is attached to the cap in a leak proof manner. The bottle may be connected—snapped or screwed on—to the breast pump and later disconnected and recapped. Alternatively, the vented cap may be threaded such that it may be loosened and removed from the bottle, thereby allowing a manual feed of either breast milk or other enteral feeding solution, all without leakage. In manual feed embodiments, the cap may be tethered to the bottle such that it is not misplaced. When the cap is removed, the breast milk or other enteral feeding solution may be poured directly into the bottle. Once capped, the bottle may be stored, frozen, and thawed with no exposure point until it is used for feeding a baby. If no vent is provided, the cap may be cracked or loosened slightly in order to begin the flow of milk.

Further embodiments provide a one-piece bottle containing enteral feeding material and having a top end with a threaded section and a bottom end comprising a funneled connector port; and a threaded cap dimensioned to mate with the threaded section of the one-piece bottle; wherein the funneled connector port connects to an enteral feeding assembly; wherein the threaded cap provides a leak proof seal such that there is no exposure point until it is used for feeding, thereby preventing contamination. In such embodiments, a bottom narrow end of the funneled connector port may terminate in a female luer lock, wherein the female luer lock is molded to the funneled connector port. A male luer lock may be attached to the female luer lock. By way of example, the male and female luer locks may comprise screw type locks or snap locks.

In some embodiments, the bottom narrow end of the funneled connector port is mechanically connected or bonded to a fluid transfer set. The fluid transfer set may comprise tubing that is attached to the funneled connector port at one end and includes a connector disposed at another end. The connector may comprise a male or female luer lock, or an oral tube port. The oral tube port may comprise a funneled connection port providing a connection to a syringe adapter enteral feeding assembly and enteral feeding device. Alternatively, the oral tube port may comprise an oral syringe connecting port, which provides attachment to an oral syringe connector of a syringe adapter feeding assembly. The oral syringe connector may comprise a clear step connector, a colored step connector, or a molded single oral connector.

In additional embodiments, the threaded cap may include a rotating section that rotates with respect to the cap such that apertures in the rotating section may be aligned with similarly dimensioned apertures in the cap. The rotating section includes a raised tab for turning the rotating section between a configuration where the apertures are aligned and a sealed configuration where the apertures are not aligned.

In other embodiments, the threaded cap may include squeeze points, wherein pressure is provides by a user at the squeeze points while rotating the cap in order to open for venting. The threaded cap locks in place when fully screwed on and vents when squeezed and cracked open.

In additional embodiments, a sealed membrane is provided on a top of the bottle, and the threaded cap includes a piercing element that pierces the sealed membrane when the cap is screwed onto the bottle. The threaded cap may further include a molded-in breakaway area for venting.

In further embodiments, the threaded section of the bottle includes pockets, and the threaded cap includes mirrored detents that provide a seal when aligned with the pockets and create vents when detached from the pockets. Alternatively, the threaded section of the bottle may include interrupted threads, wherein the threaded cap includes corresponding interrupted threads that align with the interrupted threads of the bottle for venting, but otherwise form a seal.

BRIEF DESCRIPTION OF THE DRAWINGS

The present disclosure, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability of the disclosed technology.

FIG. 2A illustrates a cross-section view of an enteral feeding connector with a positive taper funnel shaped opening, consistent with embodiments disclosed herein.

FIG. 2B illustrates a cross-section view of an enteral feeding connector without a positive taper funnel-shaped opening.

FIG. 3A illustrates an embodiment of a reservoir body as may be used in an enteral feeding system.

FIG. 3B illustrates an embodiment of reservoir liner as may be used in an enteral feeding system.

FIG. 8F illustrates a one-piece bottle having a sealed membrane, while

FIG. 8I illustrates a one-piece bottle having threads with pockets, while

FIG. 8K illustrates a one-piece bottle having interrupted threads, while

FIGS. 9A and 9B illustrate a perspective view of a modified capped reservoir comprising a one-piece bottle having an oral syringe connecting port consistent with embodiments disclosed herein.

These figures are not intended to be exhaustive or to limit the disclosed technology to the precise form disclosed. It should be understood that the disclosed technology can be practiced with modification and alteration, and that the disclosed technology be limited only by the claims and the equivalents thereof.

DETAILED DESCRIPTION

Enteral feeding systems have multiple elements and may include a combination of two or more of a reservoir body, a reservoir liner, a reservoir connector, a reservoir cap, syringe adapter enteral feeding assembly, an enteral feeding device and any other compatible device or element. An enteral feeding system may include any suitable combination of elements. The elements may be separate so long as they are connectable to form a working system. Embodiments of the present disclosure provide an enteral feeding system with a reservoir mechanically coupled to an enteral tip. The enteral tip may include a male connector and the reservoir may include a female connector configured to mechanically couple to the male connector. The male connector may include a positive taper funnel-shaped opening on its distal end such that a liquid may transfer between the reservoir and the enteral tip through the positive taper funnel-shaped opening.

Embodiments of the present disclosure may be better understood by first describing an enteral feeding system. It should be understood that the enteral feeding system described herein is only one example of an enteral feeding system, and other system configurations may be used as known in the art. Similarly, in some embodiments, the male connector may be located on the reservoir and the female connector may be located on the enteral tip.

Figure 1:
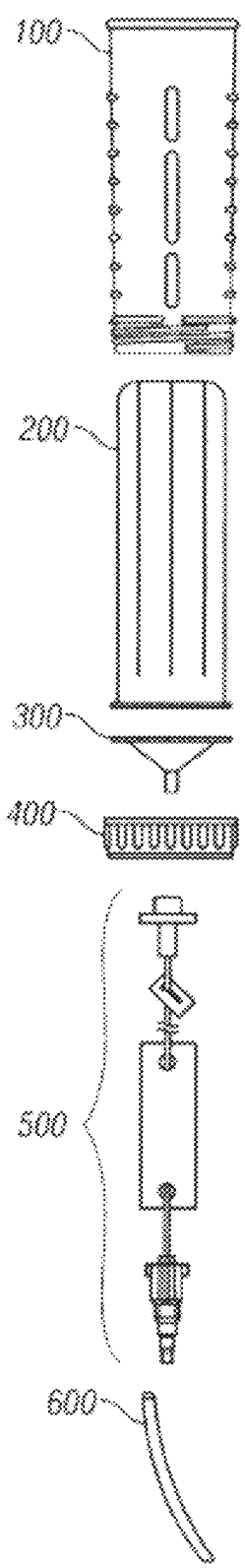
FIG. 1 is a schematic illustration of an embodiment of an enteral feeding system.

FIG. 1 illustrates an example enteral feeding system having reservoir body 100, reservoir liner 200, reservoir connector 300, reservoir cap 400, syringe adapter enteral feeding assembly 500, and enteral feeding device 600. FIG. 1 depicts the various elements of the embodiment of the system. In use, the elements may be connected in any suitable manner. In some embodiments, each connection is unique such that it will only mate and/or connect with elements of an enteral feeding system. In other embodiments, each connection prevents the enteral feeding material from substantial interaction with an environment external to the system and the patient. In various embodiments, each connection prevents the enteral feeding material from any interaction with the external environment. In addition, in some embodiments one or more of the elements is disposable. In other embodiments, each element is disposable.

FIG. 2A a cross-section view of an enteral feeding connector with a positive taper funnel shaped opening. As illustrated, the enteral feeding system may include a male enteral feeding connector 2006 and a female enteral feeding connector 2008. The female enteral feeding connector 2008 may be coupled to a distal end of a reservoir, a syringe, an intravenous bag delivery tube, or other enteral feeding container or fluid delivery apparatus. Male enteral feeding connector 2006 may be located at a proximal end of an enteral feeding delivery tip.

Female connector 2008 may include a skirt slip 2002 configured to couple to male enteral feeding connector 2006. For example, the distal and of skirt slip 2002 may include a threaded portion, either on an outer radial surface or an inner radial surface, configured to screw into, or onto, male enteral feeding connector 2006. Female enteral connector 2008 may also include a shroud skirt 2004 configured to slip over a stem member 2012 of male enteral feeding connector 2006. Male enteral feeding connector 2006 may also include an outer skirt 2014 configured to couple to skirt slip 2002 on female enteral connector 2008. In some examples, outer skirt 2014 of male enteral feeding connector 2006 may form fit, snap fit, or otherwise mechanically couple to skirt slip 2002 on female enteral connector 2008.

Stem member 2012 on male enteral feeding connector 2006 may be shaped, at its proximal end, with a positive taper funnel-shaped opening 2010. When stem number 2012 is disposed with and shroud skirt 2004, an outer radial surface at the proximal end of male member 2012 may contact or nearly contact an inner radial surface of shroud skirt 2004 as to eliminate any void or negative space there between. Accordingly, fluid may transfer between female enteral feeding connector 2008 and male enteral feeding connector 2006 without becoming stuck or redirected into a negative space or void between the two connectors. The positive tapered funnel-shaped opening 2010 is configured to promote the transfer of liquid between the two connectors.

In alternative embodiments, male enteral feeding connector 2006 may be located at the distal end of a feeding reservoir, syringe, intravenous bag, or other enteral feeding storage or delivery apparatus, and female enteral feeding connector 2008 may be located at a proximal end of an enteral feeding delivery tip. In some examples, an inner radial surface of positive tapered funnel-shaped opening 2010 may be conical. In other examples, the inner radial surface of positive tapered funnel-shaped opening 2010 may be concave or convex.

FIG. 2B a cross-section view of an enteral feeding connector without a positive taper funnel-shaped opening. As illustrated, female enteral feeding connector 2008 may include a skirt slip 2052 configured to mechanically couple to an outer skirt 2064 of male enteral feeding connector 2056. Female enteral feeding connector 2008 may also include a shroud skirt 2054 configured to slip over a stem member 2062 on male enteral feeding connector 2056. As illustrated, stem member 2062 located on male enteral feeding connector 2056 may include an opening bordered by a negative tapered outer radial surface 2060 at its proximal end. As such, when male member 2062 is disposed within shroud skirt 2054, a negative space or void may be created between an inner radial surface of shroud skirt 2054 and the outer radial surface 2060 located at the proximal land of stem member 2062. This negative space or void may trap liquid transferring between shroud skirt 2054 and male member 2062.

Figure 2C:
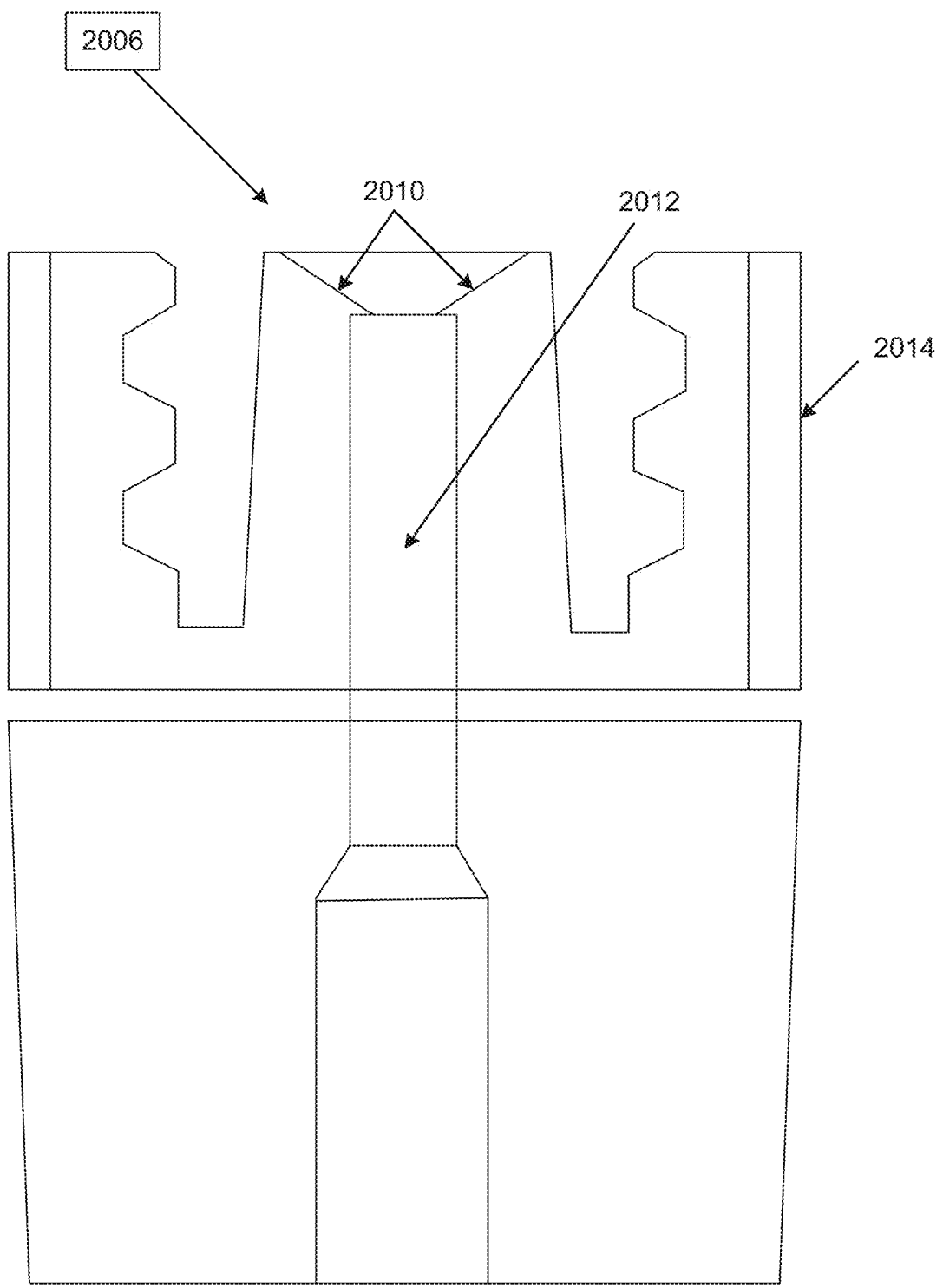
FIG. 2C illustrates a cross-section view of an enteral feeding connector with a positive taper funnel-shaped opening consistent with embodiments disclosed herein.

FIG. 2C illustrates a cross-section view of an enteral feeding connector with a positive taper funnel-shaped opening. As illustrated, male enteral feeding connector 2006 includes stem member 2012 and outer skirt 2014. The proximal end of stem member 2012 includes a positive tapered funnel-shaped opening 2010. Stem member 2012 is configured to slip inside a shroud skirt on a corresponding female enteral feeding connector, such that liquid transferring between the female enteral feeding connector and the male enteral feeding connector 2006 may pass through the shroud skirt and into the positive taper funnel-shaped opening 2010 and down the remainder of the opening located at the radial axis of the male enteral feeding connector 2006.

FIG. 3A illustrates an embodiment of reservoir body 100. Reservoir body 100 may be of any suitable size, shape and capacity and may be made of any suitable material. Reservoir body 100 may comprise a rigid material. In some embodiments, reservoir body 100 is made of plastic and has a capacity of about 10 ml to about 2000 ml. Reservoir body 100 may be cylindrical in shape, but it may have any suitable shape. Reservoir body 100 is generally hollow such that it defines an area in which reservoir liner 200 may be disposed. Reservoir body 100 has distal end 120 and proximal end 110. References to "proximal" and "distal" elements are made from the perspective of the patient (e.g., reservoir body 100 is distal to enteral feeding device 600). Proximal end 110 may be open or closed. In some embodiments, proximal end 110 includes connection structure 150. Connection structure 150 may be any structure or substance that facilitates connection between reservoir body 100 and reservoir cap 400. In the illustrated embodiment, connection structure 150 comprise threads that interact with corresponding threads 480 on reservoir cap 400 to form a connection. In some embodiments of the disclosure, distal end 120 is open. In various embodiments, reservoir body 100 has measurement indicators 130 that show the amount of material remaining within reservoir body 100.

FIG. 3B illustrates an embodiment of reservoir liner 200. Reservoir liner 200 is configured to hold and dispense enteral feeding material and may be of any suitable size, shape and capacity and may be made of any suitable material. Reservoir liner 200 may be a non-rigid and made of plastic. Reservoir liner 200 is configured to fit within reservoir body 100. Reservoir liner 200 may be substantially cylindrical with a diameter smaller than the diameter of a substantially cylindrical reservoir body 100. Reservoir liner 200 includes distal end 220 and proximal end 210. Proximal end 210 may have a lip 250 around its circumference. Lip 250 may be made of the same material as the rest of reservoir liner 200 or it may be made of a different material. Lip 250 may be sized and configured to contact proximal end 110 of reservoir body 100 when reservoir liner 200 is disposed within reservoir body 100. In such embodiments, lip 250 is also configured to contact distal end 320 of reservoir connector 300. In some embodiments, reservoir liner 200 may be physically attached to reservoir body 100. In other embodiments, reservoir liner 200 may be unitary with reservoir body 100. In various embodiments, reservoir liner 200 is pre-filled with enteral feeding material and sealed such that proximal end 320 is closed. In some such embodiments, reservoir liner 200 is sealed using a material that may be pierced or opened as reservoir cap 400 is attached to reservoir body 100.

Figure 4A:
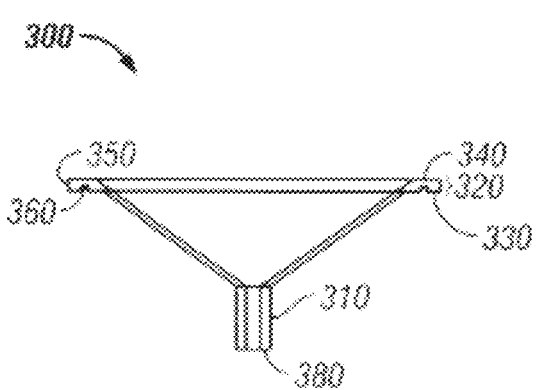
FIG. 4A illustrates a side view of an embodiment of a reservoir connector as may be used in an enteral feeding system.
Figure 4B:
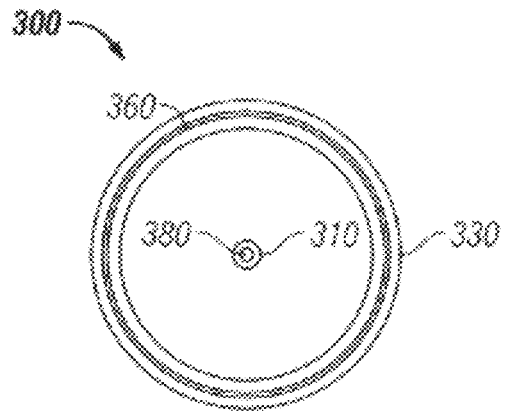
FIG. 4B illustrates a view of the proximal end of an embodiment of a reservoir connector as may be used in an enteral feeding system.

FIGS. 4A and 4B illustrate an embodiment of reservoir connector 300. Reservoir connector 300 may be of any suitable size and shape and may be made of any suitable material. In some embodiments, reservoir connector 300 may be attached to or unitary with reservoir cap 400. In such embodiments, the attachment may be made by any suitable method. In the depicted embodiment, reservoir connector 300 has distal end 320 and proximal end 310. Distal end 320 is configured to contact reservoir liner 200 and/or reservoir body 100, whereas proximal end 310 is configured to connect with syringe adapter enteral feeding assembly 500. Reservoir connector 300 may comprise a non-rigid material, such as rubber, and is tapered such that proximal end 310 has a diameter or area that is less than the diameter or area of distal end 320. In the illustrated embodiment, proximal end 310 has aperture 380 and is open at its distal end 320 such that enteral feeding material may enter through distal end 320 and pass through aperture 380. Additionally, distal end 320 includes a lip 350 having a proximal surface 330 and a distal surface 340. In some embodiments, lip 350 is generally circular, is disposed around the circumference or edge of distal end 320 and is sized and configured such that distal surface 340 will contact lip 250 of reservoir liner 200 and proximal surface 330 will contact edge 460 of reservoir cap 460. In some embodiments, proximal surface 330 of lip 350 has annular groove 360 that is configured to mate with annular bump 440 of reservoir cap 400. Reservoir connector 300 may have a structure capable of piercing or opening a reservoir liner 200 that is pre-filled with enteral feeding material and sealed at its proximal end 210.

Figure 5A:
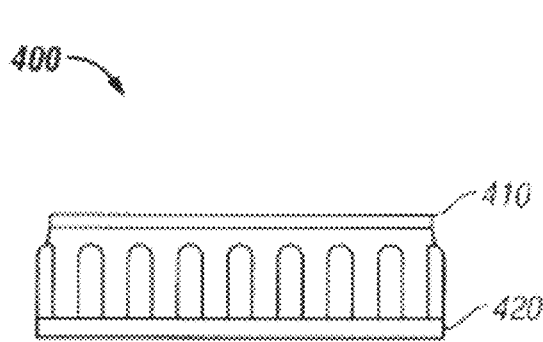
FIG. 5A is a side view of an embodiment of a reservoir cap as may be used in an enteral feeding system.
Figure 5B:
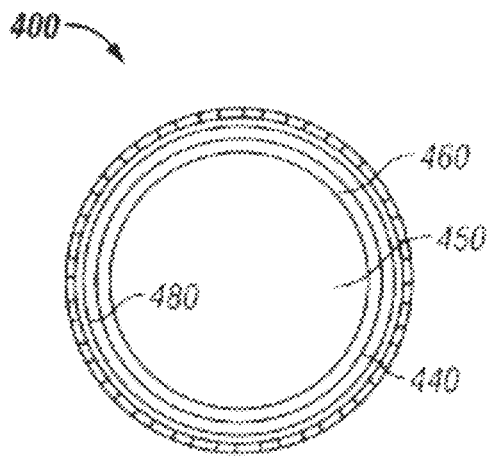
FIG. 5B is a view of the distal end of an embodiment of a reservoir cap as may be used in an enteral feeding system.

FIGS. 5A and 5B illustrate an embodiment of reservoir cap 400. Reservoir cap 400 may be any suitable size, shape and configuration and may be made of any suitable material. Reservoir cap 400 is configured to connect with reservoir body 100. In some embodiments, reservoir cap 400 may be attached to or unitary with reservoir connector 300. Reservoir cap 400 may be rigid and made of plastic. In the depicted embodiment, reservoir cap 400 has proximal end 410 having edge 460 and has distal end 420. In some embodiments, edge 460 is configured to contact the proximal surface 330 of reservoir connector 300 when reservoir cap 400 is connected to reservoir body 100. Edge 460 may have an annular bump 440 which mates with annular groove 360 of reservoir connector 300. The distal end 310 of reservoir connector may pass through opening 450 such that distal end 310 is connectable to additional elements, including syringe adapter enteral feeding assembly 500. The connection of reservoir cap 400 to reservoir body 100 may be made by interaction of connection structures 150 with threads 480. The connection of reservoir cap 400 to reservoir body 100 may cause the distal end 320 of reservoir connector 300 to contact lip 250 of reservoir liner 200. Accordingly, in some embodiments, the connection of reservoir cap 400 to reservoir body 100 secures reservoir liner 200 to reservoir body 200, secures reservoir connector 300 to reservoir liner 200 and secures reservoir connector 300 to reservoir cap 400, all in a manner that permits flow of an enteral feeding medium from reservoir liner 200 to the distal end 310 of reservoir connector 300. In some embodiments, this connection is such that the enteral feeding medium is not exposed to the external environment. In some embodiments, reservoir cap 400 may have a structure capable of piercing or opening a reservoir liner 200 that is pre-filled with enteral feeding material and sealed at its proximal end 210.

Figure 6:
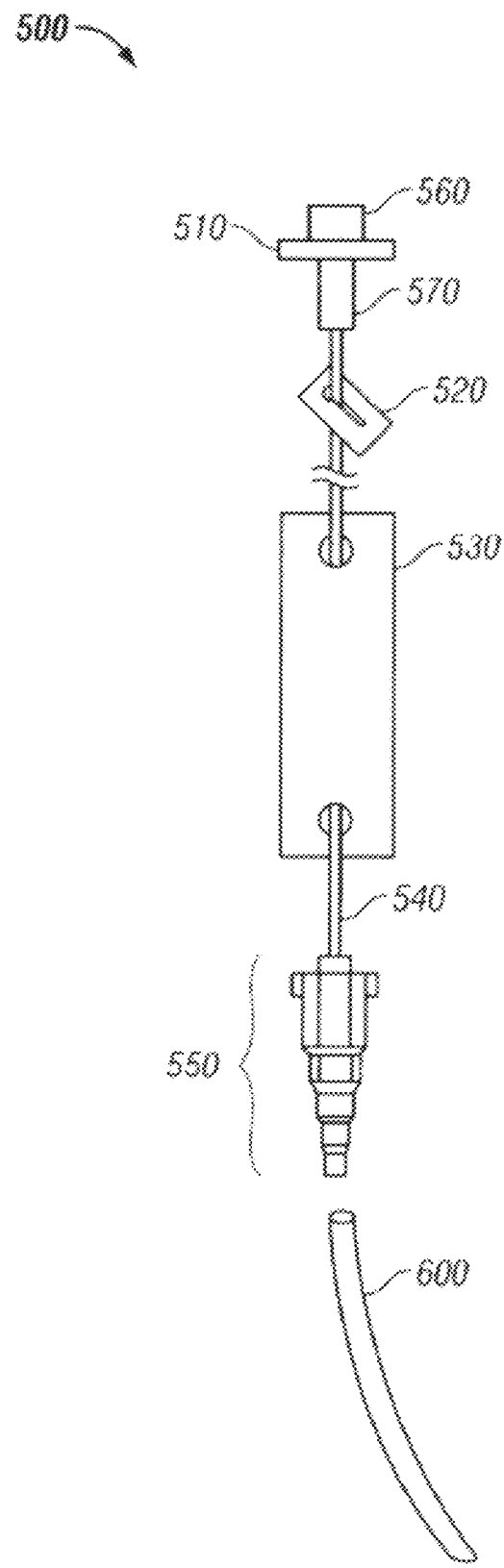
FIG. 6 is a schematic illustration of an embodiment of a syringe adapter enteral feeding assembly as may be used in an enteral feeding system.

FIG. 6 illustrates an embodiment of syringe adapter enteral feeding assembly 500. Syringe adapter enteral feeding assembly 500 may be any suitable size and may be made of any suitable material and may have various combinations of elements. The depicted embodiment features syringe adapter 510, clamp 520, warning label 530, tubing 540, and connection member 550. Syringe adapter 510 may be configured as described in U.S. Design Pat. No. D542,406, which is hereby expressly incorporated by reference in its entirety. Syringe adapter 510 may have a distal end 560 configured to connect to reservoir connector 300 and a proximal end configured to connect to tubing 540. Distal end 560 may connect to reservoir connector 300 in any suitable manner. In some embodiments, distal end 560 may connect to reservoir connector 300 in a manner that prevents exposure of the enteral feeding medium to the external environment. Clamp 520 may be any suitable clamp. In some embodiments, clamp 520 may be a roller clamp or a slide clamp. Tubing 540 may be made of any suitable material and may have any suitable width, length and thickness. In some embodiments, the tubes may be made of plastic, polyurethane or silicone. In some embodiments, warning label 530 indicates that syringe adapter enteral feeding assembly 500 is to be used for enteral feeding only.

FIG. 6 also depicts an embodiment of enteral feeding device 600. Enteral feeding device 600 may be any suitable device for any suitable method or type of enteral feeding. Enteral feeding device 600 may also include a guide wire assembly to facilitate guiding the assembly into a patient. In some embodiments, enteral feeding device 600 is a nasogastric feeding tube passed through the nares, down the esophagus and into the stomach. In other embodiments, enteral feeding device 600 is a gastric feeding tube inserted through a small incision in the abdomen into the stomach and is used for long-term enteral nutrition. The gastric tube may be any type of gastric tube, including a percutaneous endoscopic gastrostomy tube or a gastronomy tube inserted in an open procedure. In yet other embodiments, enteral feeding device 600 is a jejunostomy tube that is generally surgically inserted into the jejunum rather than the stomach. Enteral feeding device 600 may comprise a dual lumen gastrojejunostomy tube. In some dual lumen embodiments one lumen is a gastric tube and the second lumen is a jejunal lumen. In such embodiments, the gastric lumen is used for decompression and the jejunal lumen is used to administer feedings.

In some embodiments, a method of providing a patient with an enteral feeding medium is provided. The enteral feeding medium may be any material suitable for enteral feeding a patient. Such methods may include the use of a system as described herein in enteral feeding a patient. In some embodiments, the methods provide the enteral feeding medium to a patient without substantial exposure of the enteral feeding material to an external environment. Additionally, the methods may provide the enteral feeding medium to a patient without exposure to an external environment.

Figure 7:
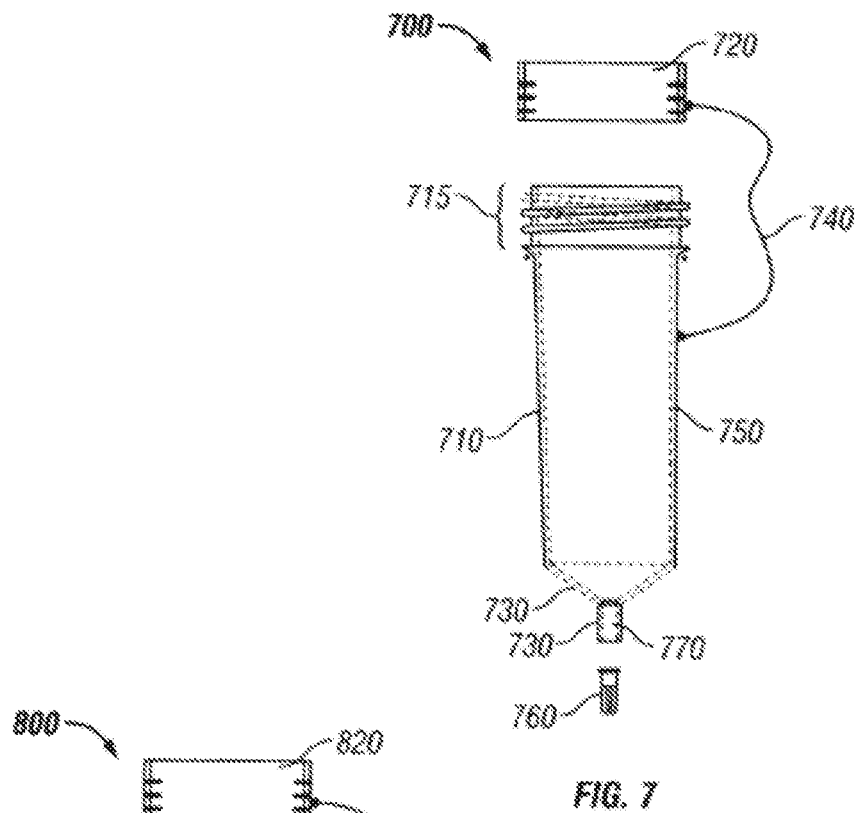
FIG. 7 illustrates a cross-sectional view of a capped reservoir comprising a one-piece bottle consistent with embodiments disclosed herein.

Referring to FIG. 7, a capped reservoir 700 is illustrated comprising a one-piece bottle 710 with no vent holes, a top end having a threaded section 715 dimensioned to mate with a threaded cap 720, and a bottom end having a funneled connector port 730, which may provide connections to an enteral feeding assembly. By way of example, the funneled connection port 730 may provide a connection to the syringe adapter enteral feeding assembly 500 and enteral feeding device 600 depicted and described with respect to FIG. 1. For such embodiments, the one-piece bottle 710 is provided in lieu of the reservoir body 100 and reservoir connector 300 of FIG. 1.

With further reference to FIG. 7, the threaded cap 720 provides a leak proof seal when tightened on the threaded section 715 of the one-piece bottle 710, and allows venting of the bottle 710 when loosened. Because the enteral feeding system comprises a closed system, venting is needed to allow the fluid to flow. In some embodiments, the cap 720 may be attached to the bottle 710 using tether 740 such that it is not misplaced. As stated, the bottom end of the one-piece bottle 710 terminates in a funneled connector port 730, which may provide connections (e.g., through the use oral syringe connectors) to an enteral feeding assembly in a manner that is not compatible with IV connections. The one-piece bottle 710 and cap 720 may be made from any suitable material. In some embodiments, one-piece bottle 710 is made of plastic and has a capacity of about 10 ml to about 2000 ml. The bottle material may be clear, partially transparent, white, orange, purple, or any other suitable color. The one-piece bottle 710 illustrated in FIG. 7 is generally cylindrical in shape, but it may have any suitable shape. In various embodiments, one-piece bottle 710 has measurement indicators that show the amount of material remaining within bottle 710.

In some embodiments, one-piece bottle 710 is generally hollow and defines an area in which a reservoir liner 750 may be disposed. The reservoir liner 750 may be configured to hold and dispense enteral feeding material and may be of any suitable size, shape, capacity and material. By way of example, reservoir liner 750 may be non-rigid and made of plastic. In some embodiments, reservoir liner 750 is substantially cylindrical with a diameter smaller than the diameter of a substantially cylindrical one-piece bottle 710. Reservoir liner 750 may be unitary with one-piece bottle 710. In various embodiments, reservoir liner 750 is sealed using a material that may be pierced or opened as cap 720 is attached to one-piece bottle 710.

With continued reference to FIG. 7, the funneled connector port 730 of one-piece bottle 710 may be of any suitable size and shape and may be made of any suitable material. In some embodiments, funneled connector port 730 includes a removable cap 760 on its bottom tip. In such embodiments, the attachment may be made by any suitable method. In the depicted embodiment, the top end of funneled connector port 730 is configured to contact reservoir liner 750 and/or one-piece bottle 710, whereas the bottom end is configured to connect with, for example, the syringe adapter enteral feeding assembly 500 illustrated in FIG. 1. Funneled connector port 730 can be made of a non-rigid material, such as rubber, and is tapered such that its bottom end has a diameter or area that is less than the diameter or area of its top end. The bottom end of the funneled connector port 730 includes an aperture 770 such that enteral feeding material may pass through aperture 770 and into the syringe adapter enteral feeding assembly 500.

Figure 8A:
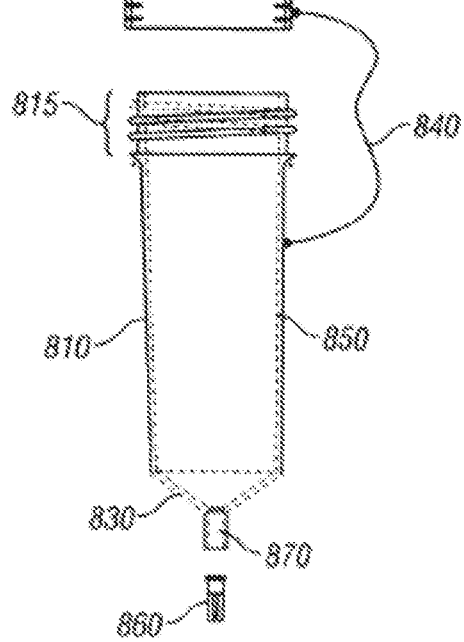
FIG. 8A illustrates a cross-sectional view of a capped reservoir comprising a one-piece bottle including a vented cap consistent with embodiments disclosed herein.
Figure 8B:
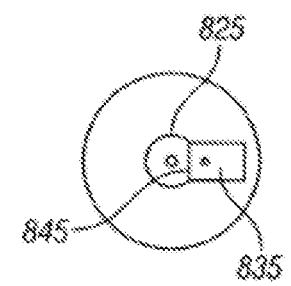
FIG. 8B illustrates a threaded bottle cap consistent with embodiments disclosed herein.

Referring to FIGS. 8A and 8B, a capped reservoir 800 is illustrated comprising a one-piece bottle 810, a top end having a threaded section 815 dimensioned to mate with a threaded cap 820 having a filtered air vent port 825, and a bottom end having a funneled connector port 830, which may provide connections to an enteral feeding assembly. Similar to the embodiment of FIG. 7, the funneled connection port 830 may provide a connection to the syringe adapter enteral feeding assembly 500 and enteral feeding device 600 depicted and described with respect to FIG. 1. In some embodiments, the cap 820 may be attached to the bottle 810 using tether 840 such that it is not misplaced.

In the illustrated embodiment, the threaded cap 820 includes filtered air vent port 825, which may be selectively closed, for example, using a snap-on seal 835 attached via a hinge 845 comprising an area of reduced thickness. In certain embodiments, the selectively closable vent port 825 may be non-filtered. In some embodiments, the closable air vent port 825 may be located on the side of the one-piece bottle 810 rather than on the cap 820. During use, the closable vent port 825 provides air compensation when opened, and provides a leak proof seal when closed. In embodiments featuring a filtered vent port 825, the air filter may or may not comprise a bacterial barrier. By way of example, the filter may comprise a 0.2 micron filter for air filtration providing significant bacterial protection. The one-piece bottle 810 is generally hollow and defines an area in which a reservoir liner 850 may be disposed. Like the embodiment of FIG. 7, the bottom end of the funneled connector port 830 includes an aperture 870 such that enteral feeding material may pass through aperture 870 and into the syringe adapter enteral feeding assembly 500. The funneled connector port 830 may include a removable cap 860 on its bottom tip.

Figure 8C:
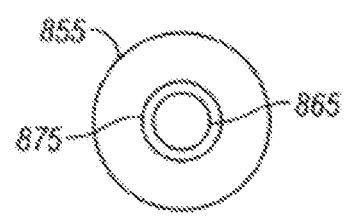
FIG. 8C illustrates an alternative bottle cap having an RFID device attached thereto consistent with embodiments disclosed herein.

In the embodiments of FIGS. 7 and 8A, the one-piece bottle may include a novel vented cap that prevents bacteria from entering the bottle. The vented cap allows the bottle to be filled with breast milk through the use of a breast pump that is attached to the cap in a leak proof manner. Additionally, the cap may be removed and the bottle may then be connected—snapped or screwed on—to the breast pump. In further embodiments, the vented cap may be threaded such that it may be loosened and removed from the bottle, thereby allowing a manual feed of either breast milk or other enteral feeding solution, all without leakage. In manual feed embodiments, the cap may be tethered to the bottle such that it is not misplaced. When the cap is removed, the breast milk or other enteral feeding solution may be poured directly into the bottle. Once capped, the bottle may be stored, frozen, and thawed with no exposure point until it is used for feeding a baby, thereby avoiding contamination. If no vent is provided, the cap may be cracked or loosened slightly in order to begin the flow of milk. Referring to FIG. 8C, in some embodiments, an alternative cap 855 may include an RFID tag 865 that is attached to the cap 855 via mounting post 875. By way of example, the RFID tag 865 may be used for mother/baby identification of appropriately matching breast milk.

Figure 8D:
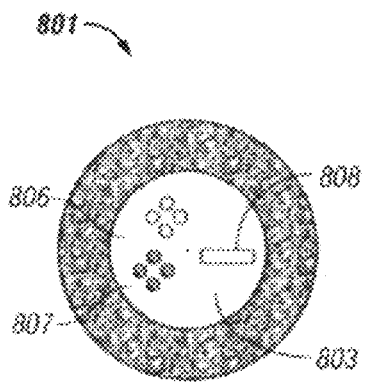
FIGS. 8D and 8E illustrate further alternative bottle caps suitable for use with the one-piece bottle of FIG. 7.
Figure 8E:
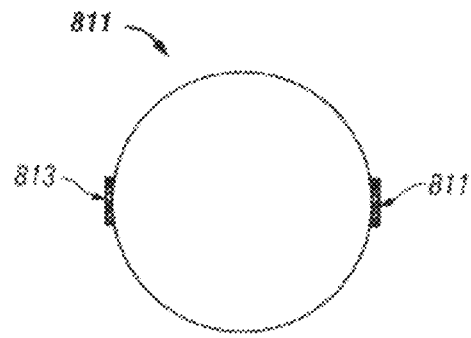

Referring to FIG. 8D, a further cap 801 suitable for use with the one-piece bottle 810 is illustrated. Cap 801 includes a rotating section 803 that rotates with respect to the cap 810 such that apertures 806 in rotating section 803 may be aligned with similarly dimensioned apertures 807 in the cap 801. Similar to a salt shaker, the rotating section 803 includes a raised section 808 for turning the rotating section 803 between a configuration where the apertures 806, 807 are aligned and a sealed configuration where the apertures 806, 807 are not aligned, as depicted in FIG. 8D. Referring to FIG. 8E, another cap 811 may include squeeze points 813, similar to a child proof pill cap, wherein pressure is provided by a user at the squeeze points 813 while rotating the cap 811 in order to open for venting. In operation, the cap 811 locks in place when fully screwed on and vents when squeezed and cracked open.

Figure 8F:
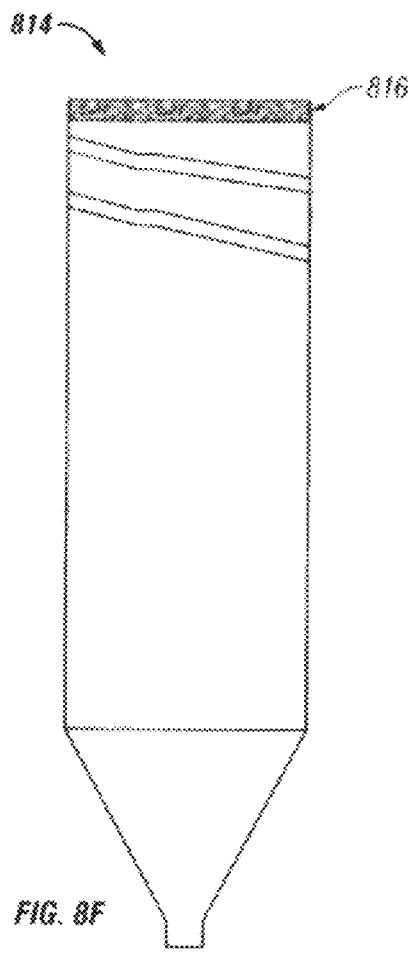
Figure 8G:
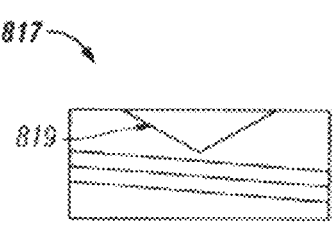
FIG. 8G illustrates a corresponding cap having a piercing element for piercing the sealed membrane.
Figure 8H:
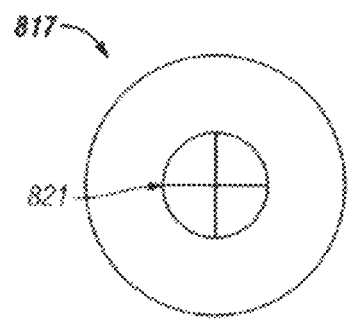
FIG. 8H illustrates a corresponding cap that includes a molded-in breakaway area for venting.

Referring to FIG. 8F, in some embodiments, a sealed membrane 816 is provided on a pre-filled or empty bottle 814. Referring to FIG. 8G, an alternative cap 817 having piercing element 819 is provided for use with the bottle of FIG. 8F having sealed membrane 816. In particular, when cap 817 is screwed into place on bottle 814, piercing element 819 is forced downward such that it pierces sealed membrane 816. Referring to FIG. 8H, cap 817 further includes a molded-in breakaway area 821 for venting. Assuming a sterile pre-filled bottle 814 is provided, there is no exposure point until it is used for feeding, thereby avoiding contamination.

Figure 8L:
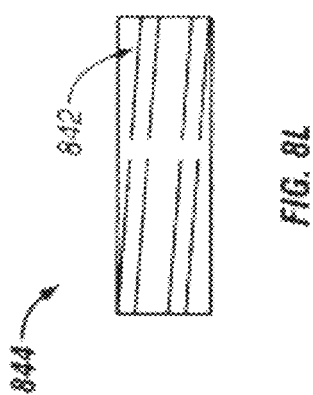
FIG. 8L illustrates a corresponding cap having interrupted threads that align with the interrupted threads of the bottle for venting, but otherwise form a seal.
Figure 8K:
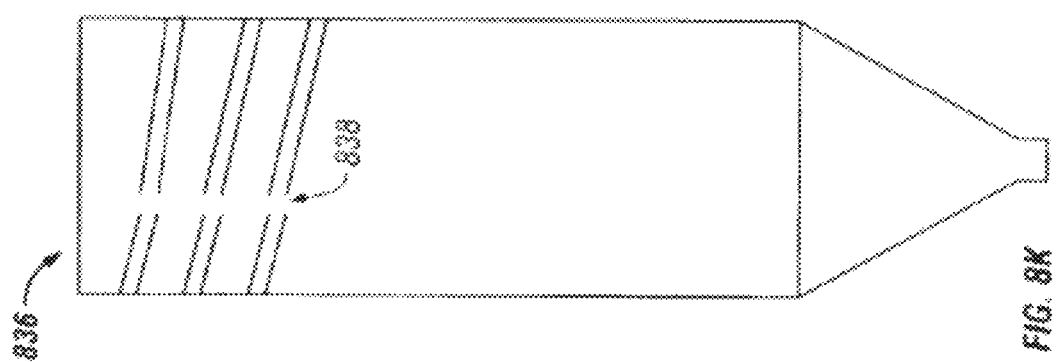
Figure 8J:
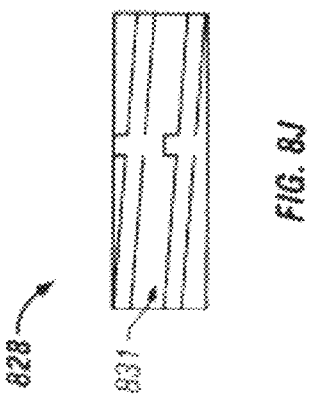
FIG. 8J illustrates a corresponding cap having mirrored detents that seal when aligned with the pockets and create vents when detached from the pockets.
Figure 8I:
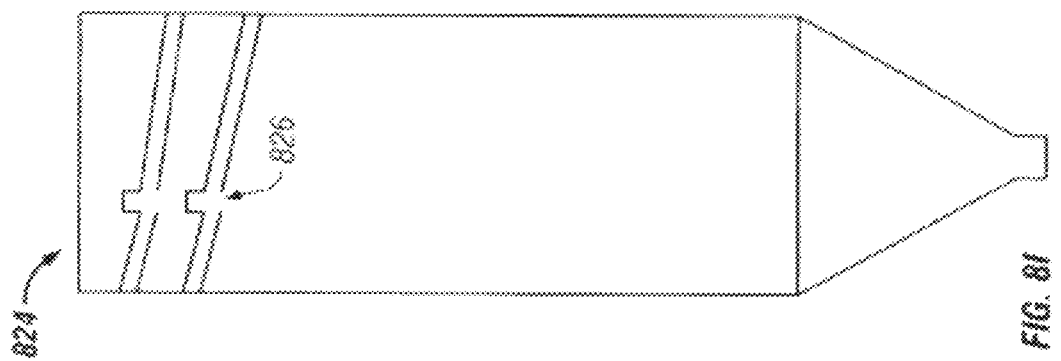

Referring to FIG. 8I, bottle 824 includes threads having pockets 826. Referring to FIG. 8J, corresponding cap 828 includes mirrored detents 831 that seal when aligned with pockets 826 and create vents when detached from pockets 826. Referring to FIG. 8K, bottle 836 includes interrupted threads 838. Referring to FIG. 8L, corresponding cap 844 includes interrupted threads 842 that align with threads 838 for venting, but otherwise form a seal. Again, assuming a sterile pre-filled bottle 824 is provided, there is no exposure point until it is used for feeding, thereby avoiding contamination Referring to FIGS. 9A and 9B, a modified capped reservoir 900 is illustrated comprising a one-piece bottle 910, a top end having a removable threaded cap 920, and a bottom end having a funneled connector port 930. An adapter comprising an oral syringe connecting port 940 is attached to the bottom end of the funneled connector port 930 such that the oral syringe connecting port 940, as an ID connection, may provide attachment to an oral syringe connector 950 of a syringe adapter feeding assembly 960. Specifically, the oral syringe connector 950 is dimensioned to slide into place within the oral syringe connecting port 940, thereby providing fluid communication with the one-piece bottle 910. FIG. 9A depicts the funneled connection port 930 connected with oral syringe stem connector 950, while FIG. 9B depicts the funneled connection port 930 disconnected from oral syringe stem connector 950. The oral syringe connecting port 940 may be molded integral with the one-piece bottle 910, or may be a separate component that is mated with the bottom end of the funneled connector port 930. In addition, the oral syringe connecting port 940 may be clear plastic, or may have any suitable color. The oral syringe stem connector 950 may comprise a clear step connector, a colored step connector, or a molded single oral connector, for example having an oral stem found on an oral syringe.

Figure 10A:
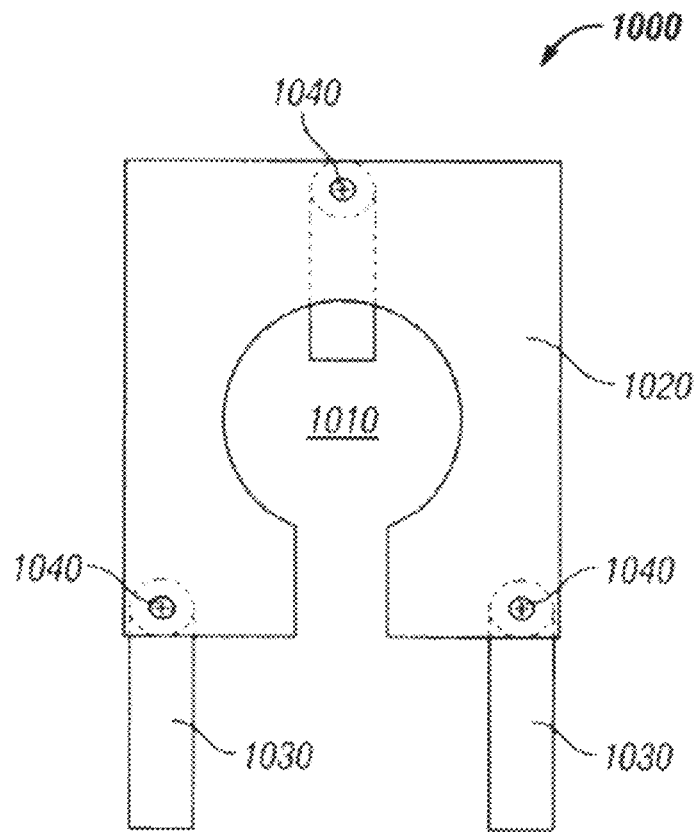
FIG. 10A illustrates a perspective view of a stand for supporting the one-piece bottles of FIGS. 7-9 consistent with embodiments disclosed herein.

Referring to FIG. 10A, some embodiments of the disclosure include a stand 1000 having a center hole 1010 for slidably receiving any of the one-piece bottles 710, 810, 910 of FIGS. 7-9. The stand 1000 is provided for supporting a one-piece bottle 710, 810, 910 in an upright position. In the illustrated embodiment, the stand 1000 includes a bottle support 1020 having center hole 1010 for receiving bottle 710, 810, 910, and a plurality of legs 1030 for supporting the bottle support 1020. The legs 1030 may be attached to the bottle support 1020 in any suitable fashion, such as using threaded fasteners 1040.

Figure 10B:
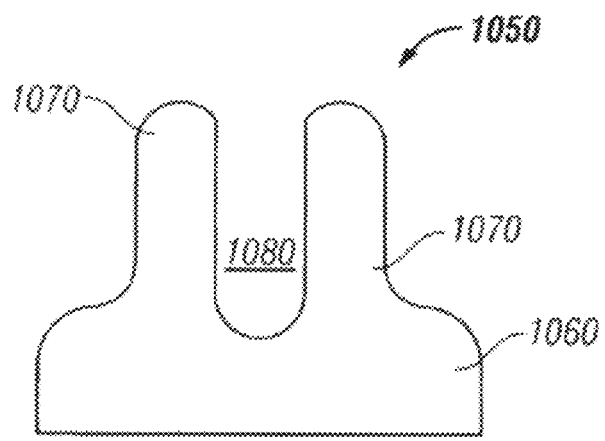
FIG. 10B illustrates a perspective view of an alternative stand for supporting the one-piece bottles of FIGS. 7-9 consistent with embodiments disclosed herein.

Referring to FIG. 10B, in further embodiments the stand may also comprise a one-piece mold 1050 having a base 1060 and two upwardly extending members 1070 forming a slot 1080 therebetween for receiving the bottle 710, 810, 910 and allowing the tubing to pass through the slot 1080. The slot 1080 may be tapered such that the bottle 710, 810, 910 slides into the slot 1080 before becoming wedged between the two members 1070.

Figure 11A:
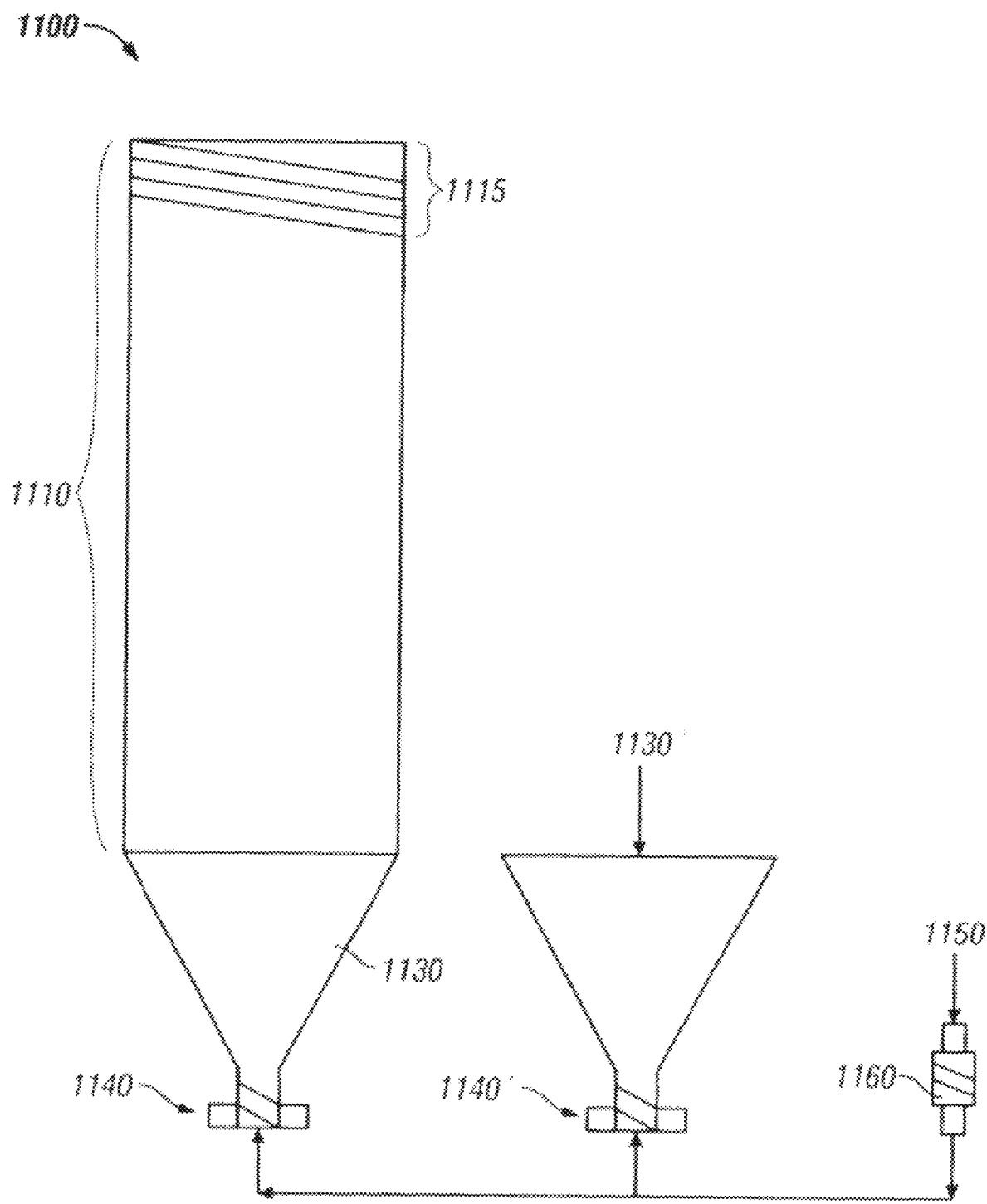
FIG. 11A illustrates a side view of a one-piece reservoir having a funneled connector port consistent with embodiments disclosed herein.

Referring to FIG. 11A, a reservoir 1100 is illustrated comprising a one-piece bottle 1110, a top end having a threaded section 1115 dimensioned to mate with a threaded cap (such as any of the threaded caps depicted in FIGS. 7 and 8), and a bottom end having a funneled connector port 1130, which may provide connections to an enteral feeding assembly. By way of example, the funneled connection port 1130 may provide a connection to the syringe adapter enteral feeding assembly 500 and enteral feeding device 600 depicted and described with respect to FIG. 1. Similar to previous embodiments, the threaded cap (not shown) provides a leak proof seal when tightened on the threaded section 1115 of the one-piece bottle 1110, and allows venting of the bottle 1110 when loosened. The funneled connector port 1130 provides connections to an enteral feeding assembly, as set forth below.

With further reference to FIG. 11A, the bottom end of the funneled connector port 1130 terminates in a female luer lock 1140. In particular, the female luer lock 1140 may be part of a one-piece mold including the bottle portion and the funneled connector port 1130. Some embodiments feature the use of a funneled connector port 1130' without an integral bottle, wherein the female luer lock 1140' may be manufactured integrally with the funneled connector port 1130' as part of a one-piece mold. Alternatively, a male luer slip or male luer lock 1150 may be molded onto the bottom end of the funneled connector port 1130, thereby replacing the female luer lock 1140 or 1140'. The male luer slip comprises the male luer lock 1150 without threaded nut 1160. Such connections can be customized based upon the IV type. By way of example, the connectors can be IV type locking connectors and/or custom sized locking connectors. Such connectors may be screw type, snap lock, or another customized type of locking connector.

Figure 11B:
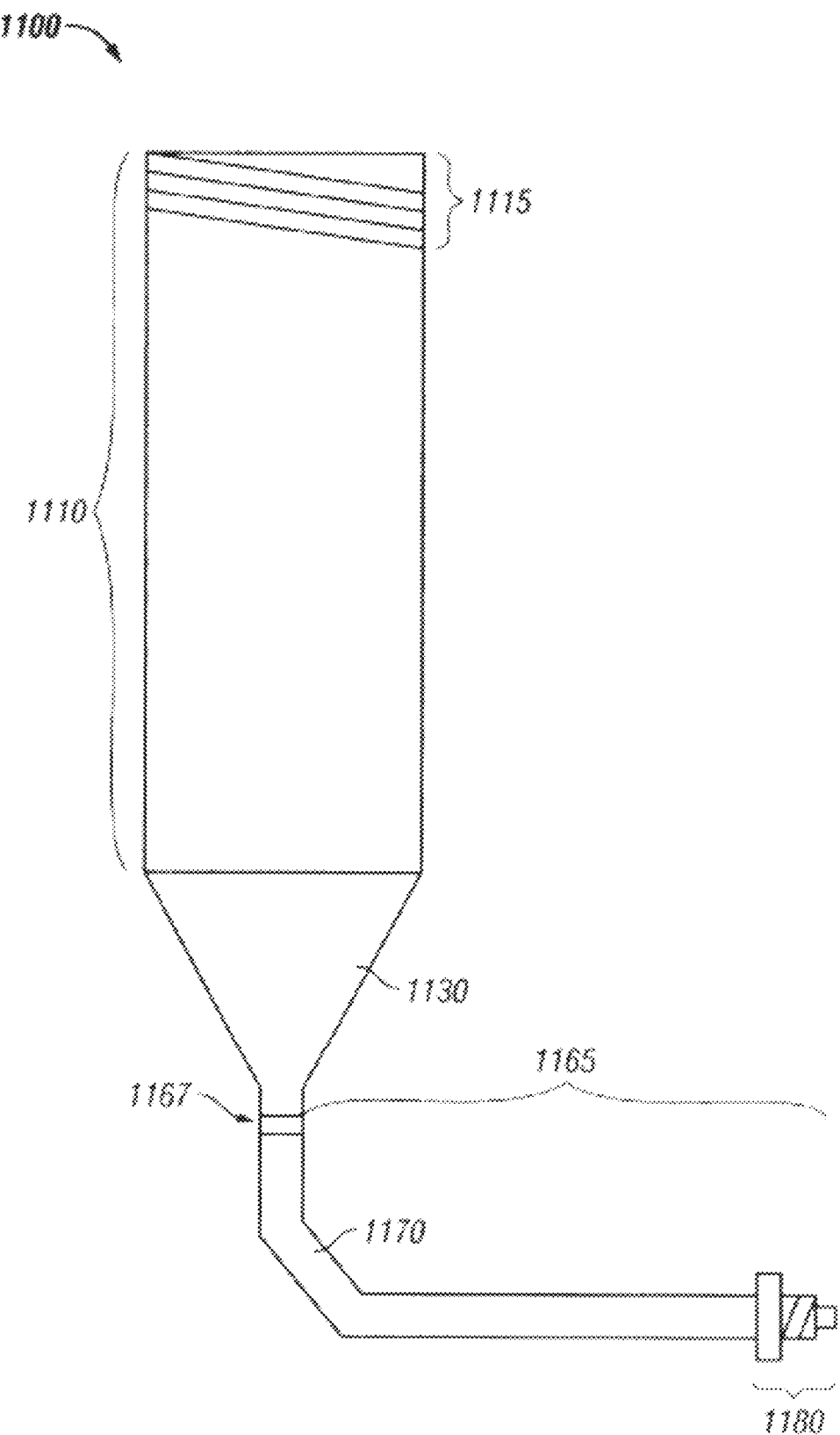
FIG. 11B illustrates a side view of a one-piece reservoir having a funneled connector port mechanically connected or bonded to a fluid transfer set consistent with embodiments disclosed herein.

Referring to FIG. 11B, in an alternative configuration, the bottom narrow end of funneled connector port 1130 is mechanically connected or bonded to a fluid transfer set 1165 at junction 1167. In the illustrated embodiment, the fluid transfer set 1165 comprises tubing 1170 with a connector 1180 disposed at the distal end. The connector 1180 may comprise a male or female luer lock, or an oral tube port. As described above with respect to FIG. 7, the oral tube port may comprise a funneled connection port 730 providing a connection to the syringe adapter enteral feeding assembly 500 and enteral feeding device 600 depicted and described with respect to FIG. 1. As described above with respect to FIG. 9, the oral tube port may alternatively comprise an oral syringe connecting port 940, such as an ID connection, which provides attachment to an oral syringe connector 950 of a syringe adapter feeding assembly 960. The oral syringe connector may comprise a clear step connector, a colored step connector, or a molded single oral connector, for example having an oral stem found on an oral syringe.

Thus, it is seen that enteral feeding systems and methods are provided. One skilled in the art will appreciate that the disclosed technology can be practiced by other than the various embodiments, which are presented in this description for purposes of illustration and not of limitation, and the present technology is limited only by the claims that follow. It is noted that equivalents for the particular embodiments discussed in this description may practice the disclosed technology as well.

While various embodiments of the present disclosure have been described above, it should be understood that they have been presented by way of example only, and not of limitation. Likewise, the various diagrams may depict an example configuration for the disclosed technology, which is done to aid in understanding the features and functionality that may be included in the disclosed technology. The disclosed technology is not restricted to the illustrated example configurations, but the desired features may be implemented using a variety of alternative configurations. Indeed, it will be apparent to one of skill in the art how alternative functional, logical or physical configurations may be implemented to implement the desired features of the present disclosure. Also, a multitude of different constituent part names other than those depicted herein may be applied to the various parts. Additionally, with regard to method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus the breadth and scope of the disclosed technology should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the disclosed technology may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, the figures and their accompanying description should not be construed as mandating a particular configuration.

The invention claimed is:

1. An enteral feeding connector, comprising:
a stem member of a male enteral feeding connector configured to fit inside a shroud skirt of a female enteral feeding connector;
wherein an end of the stem member comprises a positive taper funnel-shaped opening having a proximal end and a distal end; and
an outer radial surface of the end of the stem member is shaped to match a profile of an inner radial surface of the shroud skirt, such that the outer radial surface of the end of the stem member is flush with the inner radial surface of the shroud skirt when the stem member is disposed within the shroud skirt, and any negative space between the outer radial surface of the end of the stem member and the inner radial surface of the shroud skirt is eliminated;
wherein the positive taper funnel-shaped opening is concave in a direction from the proximal end to the distal end;
wherein the outer radial surface of the end of the stem member is uniform, such that the outer radial surface of the stem member is substantially cylindrical.

2. The enteral feeding connector of claim 1, wherein the positive taper funnel-shaped opening is conical.

3. The enteral feeding connector of claim 1, wherein the female enteral feeding connector is coupled to a distal end of an enteral feeding container or fluid delivery apparatus.

4. The enteral feeding connector of claim 3, wherein the enteral feeding container or fluid delivery apparatus comprises a reservoir, a syringe, or an intravenous bag delivery tube.

5. The enteral feeding connector of claim 1, wherein the stem member is located at a proximal end of an enteral feeding delivery tip.

6. The enteral feeding connector of claim 1, wherein the female enteral feeding connector further comprises a skirt slip configured to couple to the male enteral feeding connector.

7. The enteral feeding connector of claim 6, wherein a distal and of the skirt slip includes a threaded portion configured to screw into, or onto, the male enteral feeding connector.

8. The enteral feeding connector of claim 1, wherein the positive tapered funnel-shaped opening promotes the transfer of liquid between the female enteral feeding connector and the male enteral feeding connector.

9. An apparatus, comprising:
a female enteral feeding connector having a shroud skirt;
a male enteral feeding connector having a stem member configured to fit inside the shroud skirt, the stem member having a positive taper funnel-shaped opening having a proximal end and a distal end;
wherein an outer radial surface of the end of the stem member is shaped to match a profile of an inner radial surface of the shroud skirt and to eliminate any negative space between the outer radial surface of the end of the stem member and the inner radial surface of the shroud skirt when the stem member is disposed within the shroud skirt;
wherein the positive taper funnel-shaped opening is concave in a direction from the proximal end to the distal end;
wherein the outer radial surface of the stem member is uniform, such that the outer radial surface of the stem member is substantially cylindrical.

10. The apparatus of claim 9, wherein the outer radial surface of the end of the stem member is flush with the inner radial surface of the shroud skirt when the stem member is disposed within the shroud skirt.

11. The apparatus of claim 9, wherein the positive taper funnel-shaped opening is conical.

12. The apparatus of claim 9, wherein the female enteral feeding connector is coupled to a distal end of a reservoir, a syringe, or an intravenous bag delivery tube.

13. The apparatus of claim 9, wherein the stem member is located at a proximal end of an enteral feeding delivery tip.

14. The apparatus of claim 9, wherein the female enteral feeding connector further comprises a skirt slip configured to couple to the male enteral feeding connector.

15. The apparatus of claim 14, wherein a distal and of the skirt slip includes a threaded portion configured to screw into, or onto, the male enteral feeding connector.

16. The apparatus of claim 9, wherein the positive tapered funnel-shaped opening promotes the transfer of liquid between the female enteral feeding connector and the male enteral feeding connector.

\* \* \* \* \*